US008273791B2

(12) United States Patent
Ramirez et al.

(10) Patent No.: US 8,273,791 B2
(45) Date of Patent: Sep. 25, 2012

(54) COMPOSITIONS, KITS AND REGIMENS FOR THE TREATMENT OF SKIN, ESPECIALLY DÉCOLLETAGE

(75) Inventors: José E. Ramirez, Trumbull, CT (US); Joseph R. Faryniarz, Middlebury, CT (US)

(73) Assignee: JR Chem, LLC, Key West, FL (US)

( * ) Notice: Subject to any disclaimer, the term of this patent is extended or adjusted under 35 U.S.C. 154(b) by 796 days.

(21) Appl. No.: 12/331,781

(22) Filed: Dec. 10, 2008

(65) Prior Publication Data

US 2009/0176876 A1 Jul. 9, 2009

Related U.S. Application Data

(60) Provisional application No. 61/019,047, filed on Jan. 4, 2008.

(51) Int. Cl.
*A01N 55/02* (2006.01)
(52) U.S. Cl. ........ 514/494; 514/495; 514/500; 514/505; 514/460; 514/559; 514/725; 206/570
(58) Field of Classification Search ...................... 556/31
See application file for complete search history.

(56) References Cited

U.S. PATENT DOCUMENTS

| | | | |
|---|---|---|---|
| 46,494 | A | 2/1865 | Pike |
| 51,868 | A | 1/1866 | Schuster |
| 55,889 | A | 6/1866 | Noll |
| 81,008 | A | 8/1868 | Roemheld |
| 81,711 | A | 9/1868 | Van Wagenen |
| 87,343 | A | 3/1869 | Johnson |
| 88,973 | A | 4/1869 | McDowell |
| 92,065 | A | 6/1869 | Lighthall |
| 93,300 | A | 8/1869 | Hall et al. |
| 116,875 | A | 7/1871 | Shannon |
| 124,751 | A | 3/1872 | Lauer |
| 127,925 | A | 6/1872 | Roskopf |
| 128,385 | A | 6/1872 | Goffinet |
| 145,749 | A | 6/1873 | Pawlewski et al. |
| 140,768 | A | 7/1873 | Fisher |
| 143,133 | A | 9/1873 | Fehr |
| 149,857 | A | 1/1874 | Halpen |
| 173,607 | A | 6/1875 | Fehr |
| 171,875 | A | 1/1876 | Sievers |
| 209,331 | A | 6/1878 | Littleton |
| 229,014 | A | 6/1880 | Sharetts |
| 232,807 | A | 10/1880 | Dennett |
| 238,015 | A | 2/1881 | Yater |
| 264,783 | A | 9/1882 | Squier |
| 277,221 | A | 5/1883 | Buse |
| 284,335 | A | 9/1883 | Scott |
| 318,468 | A | 5/1885 | Haley |
| 320,836 | A | 6/1885 | Bisaillon |
| 411,657 | A | 9/1889 | Grosbety |
| 415,208 | A | 11/1889 | Johson |
| 430,048 | A | 6/1890 | Wainwright |
| 432,611 | A | 7/1890 | Hall |
| 627,296 | A | 6/1899 | Camnitzer |
| 928,539 | A | 7/1909 | Pucciarelli |
| 944,738 | A | 12/1909 | Loose |
| 992,937 | A | 5/1911 | Brodbeck et al. |
| 1,059,841 | A | 4/1913 | Crookes |
| 1,086,900 | A | 2/1914 | David |
| 1,332,190 | A | 2/1920 | Hull |
| 1,411,577 | A | 4/1922 | Mullins et al. |
| 1,488,097 | A | 3/1924 | Creger |
| 1,584,173 | A | 5/1926 | Holzapfel |
| 1,593,485 | A | 7/1926 | Crosnier |
| 1,627,963 | A | 5/1927 | Fuller |
| 1,809,082 | A | 6/1931 | Urkov et al. |
| 1,908,176 | A | 5/1933 | Osterberg |
| 1,947,568 | A | 2/1934 | Noonan |
| 1,949,797 | A | 3/1934 | Kaufmann |
| 1,982,148 | A | 11/1934 | Zimbron, Jr. |
| 2,002,829 | A | 5/1935 | Osterberg |
| 2,054,989 | A | 9/1936 | Moore |
| 2,087,162 | A | 7/1937 | Moore |
| 2,095,092 | A | 10/1937 | Barton |
| 2,114,490 | A | 4/1938 | Harris |
| 2,129,836 | A | 9/1938 | Goodman |
| 2,153,653 | A | 4/1939 | Stux |
| 2,194,218 | A | 3/1940 | Thurstan |
| 2,223,142 | A | 11/1940 | Weirich |
| 2,241,331 | A | 5/1941 | Shelton |
| 2,254,636 | A | 9/1941 | Vangunten |
| 2,267,739 | A | 12/1941 | Kemppe |
| 2,289,125 | A | 7/1942 | Keil |
| 2,299,604 | A | 10/1942 | Weirich |
| 2,344,830 | A | 3/1944 | Mohs |
| 2,361,161 | A | 10/1944 | Anderson |
| 2,370,561 | A | 2/1945 | Mecca |
| 2,372,807 | A | 4/1945 | Brown |
| 2,376,884 | A | 5/1945 | Schwenk et al. |
| 2,377,188 | A | 5/1945 | Schwenk et al. |
| 2,420,271 | A | 5/1947 | Travis et al. |
| 2,420,389 | A | 5/1947 | Travis et al. |
| 2,469,228 | A | 5/1949 | Gertler |
| 2,527,686 | A | 10/1950 | Sandberg |
| 2,556,567 | A | 6/1951 | Wright |
| 2,602,039 | A | 8/1952 | Wershaw |
| 2,649,398 | A | 8/1953 | Wright et al. |
| 2,652,355 | A | 9/1953 | Ercoli et al. |
| 2,673,364 | A | 3/1954 | Divelcy |
| 2,703,777 | A | 3/1955 | Feinstein et al. |

(Continued)

FOREIGN PATENT DOCUMENTS

EP 0 688 204 B1 12/1995

(Continued)

OTHER PUBLICATIONS

Chatterjee et al, Angewnandte, 1990, 181, 93-101.*

(Continued)

*Primary Examiner* — James D Anderson
*Assistant Examiner* — Ibrahim D Bori
(74) *Attorney, Agent, or Firm* — Carter, Deluca, Farrell & Schmidt, LLP

(57) ABSTRACT

Compositions, kits and regimens for treatment of damaged skin, especially décolletage, include application of a retinoid, hydroquinone or hydroquinone derivatives, and a composition containing a multi-metal complex.

18 Claims, No Drawings

U.S. PATENT DOCUMENTS

| | | | |
|---|---|---|---|
| 2,736,681 A | 2/1956 | Tishler | |
| 2,748,781 A | 6/1956 | Collat | |
| 2,838,440 A | 6/1958 | Thurmon | |
| 2,843,522 A | 7/1958 | Mahon | |
| 2,846,322 A | 8/1958 | Buchalter | |
| 2,870,150 A | 1/1959 | Wright et al. | |
| 2,870,151 A | 1/1959 | Wright et al. | |
| 2,872,372 A | 2/1959 | Hull | |
| 2,991,224 A | 7/1961 | Bell | |
| 3,013,883 A | 12/1961 | Welcker et al. | |
| 3,033,755 A | 5/1962 | Otto | |
| 3,035,988 A | 5/1962 | Cohen | |
| 3,084,105 A | 4/1963 | Slodki | |
| 3,137,622 A | 6/1964 | Mueller et al. | |
| 3,366,114 A | 6/1964 | Kanter | |
| 3,146,168 A | 8/1964 | Battista | |
| 3,164,523 A | 1/1965 | Fox et al. | |
| 3,184,376 A | 5/1965 | Degoli | |
| 3,210,248 A | 10/1965 | Feldmann et al. | |
| 3,215,599 A | 11/1965 | Thau et al. | |
| 3,255,079 A | 6/1966 | Schroeder et al. | |
| 3,290,218 A | 12/1966 | de Jong | |
| 3,317,372 A | 5/1967 | Hart | |
| 3,590,123 A | 6/1971 | Mclloh et al. | |
| 3,749,772 A | 7/1973 | Cardarelli et al. | |
| 3,755,560 A | 8/1973 | Dickert et al. | |
| 3,821,370 A | 6/1974 | Tenta | |
| 3,821,371 A | 6/1974 | Battista | |
| 3,826,845 A | 7/1974 | Suyama et al. | |
| 3,856,934 A | 12/1974 | Kligman | |
| 3,856,941 A | 12/1974 | Turner | |
| 3,896,238 A | 7/1975 | Smith | |
| 3,903,268 A | 9/1975 | Balassa | |
| 3,949,072 A | 4/1976 | Tenta | |
| 4,048,300 A | 9/1977 | Tomlinson et al. | |
| 4,100,269 A | 7/1978 | Pader | |
| 4,136,166 A | 1/1979 | Barnett et al. | |
| 4,138,477 A | 2/1979 | Gaffar | |
| 4,146,607 A | 3/1979 | Ritchey | |
| 4,154,911 A | 5/1979 | Bak et al. | |
| 4,160,821 A | 7/1979 | Sipos | |
| 4,161,526 A | 7/1979 | Gorman | |
| 4,166,108 A | 8/1979 | Brown et al. | |
| 4,226,851 A | 10/1980 | Sompayrac | |
| 4,226,889 A | 10/1980 | Yuhas | |
| 4,229,427 A | 10/1980 | Whitehouse | |
| 4,229,430 A | 10/1980 | Fahim et al. | |
| 4,229,437 A | 10/1980 | Likens et al. | |
| 4,255,418 A | 3/1981 | Bailey | |
| 4,273,763 A | 6/1981 | Horrobin | |
| 4,285,967 A | 8/1981 | Gubernick et al. | |
| 4,291,025 A | 9/1981 | Pellico | |
| 4,298,601 A | 11/1981 | Howard | |
| 4,302,447 A | 11/1981 | Horrobin | |
| 4,305,842 A | 12/1981 | Asakawa et al. | |
| 4,309,989 A | 1/1982 | Fahim | |
| 4,310,516 A | 1/1982 | Chang et al. | |
| 4,315,916 A | 2/1982 | Likens et al. | |
| 4,322,400 A | 3/1982 | Yuhas | |
| 4,330,527 A | 5/1982 | Arima et al. | |
| 4,331,653 A | 5/1982 | Brown et al. | |
| 4,335,110 A | 6/1982 | Collins | |
| 4,349,536 A | 9/1982 | Hausler | |
| 4,372,296 A | 2/1983 | Fahim | |
| 4,375,968 A | 3/1983 | Manhart | |
| 4,376,115 A | 3/1983 | McCrorey | |
| 4,395,398 A | 7/1983 | Yamamoto | |
| 4,406,881 A | 9/1983 | Ladanyi | |
| 4,421,769 A | 12/1983 | Dixon et al. | |
| 4,428,933 A | 1/1984 | King | |
| 4,430,324 A | 2/1984 | Viccaro | |
| 4,444,755 A | 4/1984 | Horrobin | |
| 4,465,666 A | 8/1984 | Lukas et al. | |
| 4,466,955 A | 8/1984 | Calvo et al. | |
| 4,469,684 A | 9/1984 | Higgins et al. | |
| 4,477,439 A | 10/1984 | D'Alelio | |
| 4,486,488 A | 12/1984 | Pietsch et al. | |
| 4,503,037 A | 3/1985 | Szijjarto et al. | |
| 4,512,978 A | 4/1985 | Inwood | |
| 4,515,779 A | 5/1985 | Elliott | |
| 4,522,806 A | 6/1985 | Muhlemann et al. | |
| 4,526,779 A | 7/1985 | Hashimoto | |
| 4,568,540 A | 2/1986 | Asano et al. | |
| 4,604,234 A | 8/1986 | Fujii et al. | |
| 4,606,920 A | 8/1986 | Walter | |
| 4,647,452 A | 3/1987 | Ritchey et al. | |
| 4,652,444 A | 3/1987 | Maurer | |
| 4,654,213 A | 3/1987 | Ramirez et al. | |
| 4,661,354 A | 4/1987 | Finnerty | |
| 4,665,054 A | 5/1987 | Pickart | |
| 4,678,664 A | 7/1987 | Schmolka | |
| 4,683,133 A | 7/1987 | Southard | |
| 4,708,864 A | 11/1987 | Maurer | |
| 4,713,242 A | 12/1987 | Trenzeluk | |
| 4,760,051 A | 7/1988 | Pickart | |
| 4,762,715 A | 8/1988 | Lukas et al. | |
| 4,767,753 A | 8/1988 | Pickart | |
| 4,792,443 A | 12/1988 | Filomeno | |
| 4,810,693 A | 3/1989 | Pickart | |
| 4,816,254 A | 3/1989 | Moss | |
| 4,847,083 A | 7/1989 | Clark | |
| 4,849,211 A | 7/1989 | Schrauzer | |
| 4,855,138 A | 8/1989 | Trenzeluk | |
| 4,863,987 A | 9/1989 | Hoshino et al. | |
| 4,874,361 A | 10/1989 | Obagi | |
| 4,877,770 A | 10/1989 | Pickart | |
| 4,895,727 A | 1/1990 | Allen | |
| 4,911,932 A | 3/1990 | Clum et al. | |
| 4,937,230 A | 6/1990 | Pickart | |
| 4,938,969 A | 7/1990 | Schinitsky et al. | |
| 4,956,354 A | 9/1990 | Gutierrez | |
| RE33,512 E | 1/1991 | Ramirez et al. | |
| 4,992,259 A | 2/1991 | Schiraldi et al. | |
| 5,000,944 A | 3/1991 | Prencipe et al. | |
| 5,023,237 A | 6/1991 | Pickart | |
| 5,059,588 A | 10/1991 | Pickart | |
| 5,075,469 A | 12/1991 | Chevion | |
| 5,079,010 A | 1/1992 | Natterer | |
| 5,091,171 A | 2/1992 | Yu et al. | |
| 5,091,193 A | 2/1992 | Enjolras et al. | |
| 5,093,099 A | 3/1992 | Haishi et al. | |
| 5,104,644 A | 4/1992 | Douglas | |
| 5,118,665 A | 6/1992 | Pickart | |
| 5,120,831 A | 6/1992 | Pickart | |
| 5,135,913 A | 8/1992 | Pickart | |
| 5,143,763 A | 9/1992 | Yamada et al. | |
| 5,145,838 A | 9/1992 | Pickart | |
| 5,154,932 A | 10/1992 | Burba, III et al. | |
| 5,164,367 A | 11/1992 | Pickart | |
| 5,165,914 A | 11/1992 | Vlock | |
| 5,166,176 A | 11/1992 | Obagi et al. | |
| 5,174,990 A | 12/1992 | Douglas | |
| 5,177,061 A | 1/1993 | Pickart | |
| 5,209,932 A | 5/1993 | Nichols | |
| 5,214,032 A | 5/1993 | Pickart | |
| 5,227,156 A | 7/1993 | Wiese | |
| 5,232,691 A | 8/1993 | Lemole | |
| 5,240,696 A | 8/1993 | Van Der Ouderaa et al. | |
| 5,244,651 A | 9/1993 | Kayane et al. | |
| 5,258,183 A | 11/1993 | Grimberg | |
| 5,310,546 A | 5/1994 | Douglas | |
| 5,330,748 A | 7/1994 | Winston et al. | |
| 5,330,749 A | 7/1994 | Giacin et al. | |
| 5,348,943 A | 9/1994 | Pickart | |
| 5,352,438 A | 10/1994 | N'Guyen et al. | |
| 5,382,431 A | 1/1995 | Pickart | |
| 5,385,727 A | 1/1995 | Winston et al. | |
| 5,401,730 A | 3/1995 | Sauvage et al. | |
| 5,424,077 A | 6/1995 | Lajoie | |
| 5,439,863 A | 8/1995 | Bottcher et al. | |
| 5,455,023 A | 10/1995 | Giacin et al. | |
| 5,466,470 A | 11/1995 | Lajoie | |
| 5,480,975 A | 1/1996 | Goldberg et al. | |
| 5,482,720 A | 1/1996 | Murphy et al. | |
| 5,484,597 A | 1/1996 | Slavtcheff et al. | |
| 5,496,539 A | 3/1996 | Mobley et al. | |
| 5,500,448 A | 3/1996 | Cummins et al. | |

| Patent No. | Date | Name |
|---|---|---|
| 5,523,077 A | 6/1996 | Pawelek et al. |
| 5,547,676 A | 8/1996 | Rocher et al. |
| 5,550,183 A | 8/1996 | Pickart |
| 5,552,147 A | 9/1996 | Znaiden et al. |
| 5,554,375 A | 9/1996 | Pickart |
| 5,554,647 A | 9/1996 | Perricone |
| 5,597,550 A | 1/1997 | Mo |
| 5,597,552 A | 1/1997 | Herms et al. |
| 5,616,313 A | 4/1997 | Williams et al. |
| 5,621,006 A | 4/1997 | Yu et al. |
| 5,622,724 A | 4/1997 | Bryce-Smith |
| 5,624,675 A | 4/1997 | Kelly |
| 5,631,013 A | 5/1997 | Bergmann et al. |
| 5,632,972 A | 5/1997 | Williams et al. |
| 5,645,840 A | 7/1997 | Lajoie et al. |
| 5,663,213 A | 9/1997 | Jones et al. |
| 5,686,083 A | 11/1997 | Chamness |
| 5,688,492 A | 11/1997 | Galley et al. |
| 5,690,967 A | 11/1997 | Yu et al. |
| 5,696,169 A | 12/1997 | Otsu et al. |
| 5,698,184 A | 12/1997 | Pickart |
| 5,707,609 A | 1/1998 | Mo |
| 5,708,023 A | 1/1998 | Modak et al. |
| 5,728,404 A | 3/1998 | Von Rheinbaben et al. |
| 5,747,005 A | 5/1998 | Barels et al. |
| 5,753,637 A | 5/1998 | Fried |
| 5,762,945 A | 6/1998 | Ashley et al. |
| 5,780,020 A | 7/1998 | Peterson et al. |
| 5,795,574 A | 8/1998 | Breton et al. |
| 5,798,121 A | 8/1998 | Cauwet et al. |
| 5,827,884 A | 10/1998 | Obagi et al. |
| 5,837,270 A | 11/1998 | Burgess |
| 5,855,873 A | 1/1999 | Yam |
| 5,858,335 A | 1/1999 | Lucas et al. |
| 5,858,371 A | 1/1999 | Singh et al. |
| 5,858,993 A | 1/1999 | Pickart |
| 5,861,143 A | 1/1999 | Peterson et al. |
| 5,861,144 A | 1/1999 | Peterson et al. |
| 5,861,145 A | 1/1999 | Lucas et al. |
| 5,861,146 A | 1/1999 | Peterson et al. |
| 5,861,147 A | 1/1999 | Dodd et al. |
| 5,871,718 A | 2/1999 | Lucas et al. |
| 5,871,719 A | 2/1999 | Lucas et al. |
| 5,874,067 A | 2/1999 | Lucas et al. |
| 5,874,070 A | 2/1999 | Trinh et al. |
| 5,879,666 A | 3/1999 | Lucas et al. |
| 5,882,638 A | 3/1999 | Dodd et al. |
| 5,886,184 A | 3/1999 | Dolling et al. |
| 5,888,515 A | 3/1999 | Albert et al. |
| 5,888,522 A | 3/1999 | Pickart |
| 5,897,854 A | 4/1999 | Lucas et al. |
| 5,897,855 A | 4/1999 | Trinh et al. |
| 5,897,856 A | 4/1999 | Trinh et al. |
| 5,904,921 A | 5/1999 | Bresson-Rival et al. |
| 5,911,976 A | 6/1999 | Trinh et al. |
| 5,928,631 A | 7/1999 | Lucas et al. |
| 5,928,658 A | 7/1999 | Kishida et al. |
| 5,935,608 A | 8/1999 | Fujikawa et al. |
| 5,942,214 A | 8/1999 | Lucas et al. |
| 5,948,390 A | 9/1999 | Nelson et al. |
| 5,951,990 A | 9/1999 | Ptchelintsev |
| 5,955,067 A | 9/1999 | Oge et al. |
| 5,961,993 A | 10/1999 | Boussouira et al. |
| 5,965,137 A | 10/1999 | Petrus |
| 5,965,610 A | 10/1999 | Modak et al. |
| 5,972,999 A | 10/1999 | Murad |
| 5,980,477 A | 11/1999 | Kelly |
| 5,994,403 A | 11/1999 | Donatiello |
| 6,019,976 A | 2/2000 | Bryant |
| 6,022,565 A | 2/2000 | Albert et al. |
| 6,030,605 A | 2/2000 | D'Ameila et al. |
| 6,037,386 A | 3/2000 | Modak et al. |
| 6,046,178 A | 4/2000 | Silvetti, Sr. |
| 6,060,079 A | 5/2000 | Freeman et al. |
| 6,071,543 A | 6/2000 | Thornfeldt |
| 6,083,490 A | 7/2000 | Ellis et al. |
| 6,086,666 A | 7/2000 | Noguchi et al. |
| 6,103,247 A | 8/2000 | Boussouira et al. |
| 6,103,273 A | 8/2000 | Antoun |
| 6,113,636 A | 9/2000 | Ogle |
| 6,121,254 A | 9/2000 | Saint-Leger |
| 6,123,925 A | 9/2000 | Barry et al. |
| 6,132,743 A | 10/2000 | Kuroda et al. |
| 6,143,318 A | 11/2000 | Gilchrist et al. |
| 6,149,947 A | 11/2000 | Hon et al. |
| 6,183,785 B1 | 2/2001 | Westfall |
| 6,190,407 B1 | 2/2001 | Ogle et al. |
| 6,191,167 B1 | 2/2001 | Yu et al. |
| 6,200,580 B1 | 3/2001 | Horino et al. |
| 6,200,680 B1 | 3/2001 | Takeda et al. |
| 6,217,914 B1 | 4/2001 | Meisner |
| 6,221,403 B1 | 4/2001 | Nesbit |
| 6,224,896 B1 | 5/2001 | Redmond |
| 6,248,370 B1 | 6/2001 | Harris |
| 6,261,574 B1 | 7/2001 | Costello |
| 6,267,782 B1 | 7/2001 | Ogle et al. |
| 6,287,541 B1 | 9/2001 | Creeth et al. |
| 6,303,651 B1 | 10/2001 | Hersh |
| 6,322,588 B1 | 11/2001 | Ogle et al. |
| 6,322,820 B1 | 11/2001 | Simoneau |
| 6,331,567 B1 | 12/2001 | Watson et al. |
| 6,361,800 B1 | 3/2002 | Cooper et al. |
| 6,375,942 B1 | 4/2002 | Rico |
| 6,395,301 B1 | 5/2002 | Cantin |
| 6,416,744 B1 | 7/2002 | Robinson et al. |
| 6,444,699 B2 | 9/2002 | Meisner |
| 6,451,294 B1 | 9/2002 | Simon |
| 6,471,972 B1 | 10/2002 | Bonte et al. |
| 6,475,526 B1 | 11/2002 | Smith |
| 6,497,860 B1 | 12/2002 | Kawato et al. |
| 6,517,849 B1 | 2/2003 | Seger et al. |
| 6,521,265 B1 | 2/2003 | Patterson |
| 6,558,710 B1 | 5/2003 | Godfrey |
| 6,579,541 B2 | 6/2003 | Antelman |
| 6,582,684 B1 | 6/2003 | Abrahamson |
| 6,582,710 B2 | 6/2003 | Deckers et al. |
| 6,592,852 B1 | 7/2003 | Ryles et al. |
| 6,599,513 B2 | 7/2003 | Deckers et al. |
| 6,607,716 B1 | 8/2003 | Smith et al. |
| 6,627,178 B1 | 9/2003 | Cawthon |
| 6,660,306 B2 | 12/2003 | Peshoff |
| 6,663,852 B2 | 12/2003 | Simon |
| 6,680,073 B1 | 1/2004 | Tarbet |
| 6,682,720 B2 | 1/2004 | Ryles et al. |
| 6,696,071 B2 | 2/2004 | Kelly |
| 6,699,464 B1 | 3/2004 | Popp et al. |
| 6,726,919 B2 | 4/2004 | Pace et al. |
| 6,730,309 B2 | 5/2004 | Horino |
| 6,730,329 B1 | 5/2004 | Smith |
| 6,743,416 B2 | 6/2004 | Riedl |
| 6,750,209 B1 | 6/2004 | Hudson et al. |
| 6,773,698 B2 | 8/2004 | Melinte et al. |
| 6,780,439 B2 | 8/2004 | Wilk |
| 6,800,301 B2 | 10/2004 | Smith |
| 6,833,362 B2 | 12/2004 | Bowen, Jr. et al. |
| 6,844,012 B1 | 1/2005 | Forceville et al. |
| 6,849,277 B2 | 2/2005 | Roig |
| 6,855,341 B2 | 2/2005 | Smith |
| 6,858,201 B2 | 2/2005 | Pickart |
| 6,929,800 B2 | 8/2005 | Salman |
| 6,932,976 B2 | 8/2005 | Brooks |
| 6,939,568 B2 | 9/2005 | Burrell et al. |
| 6,942,878 B2 | 9/2005 | Ishii et al. |
| 6,949,248 B2 | 9/2005 | Nishihama |
| 6,949,249 B2 | 9/2005 | Healy et al. |
| 6,964,782 B1 | 11/2005 | Smith et al. |
| 6,979,468 B1 | 12/2005 | Pollard |
| 6,989,156 B2 | 1/2006 | Gillis |
| 7,008,647 B2 | 3/2006 | Burrell et al. |
| 7,014,870 B1 | 3/2006 | Hon et al. |
| 7,026,308 B1 | 4/2006 | Gavin et al. |
| 7,049,339 B2 | 5/2006 | Thomson |
| 7,687,650 B2 | 3/2010 | Ramirez et al. |
| 2001/0014356 A1 | 8/2001 | Yoshida et al. |
| 2001/0041193 A1 | 11/2001 | Meisner |
| 2002/0001629 A1 | 1/2002 | Voellmy |
| 2002/0031557 A1 | 3/2002 | Meisner |
| 2002/0114847 A1 | 8/2002 | Peshoff |

| | | |
|---|---|---|
| 2002/0182244 A1 | 12/2002 | Jackson |
| 2003/0004564 A1 | 1/2003 | Elkins et al. |
| 2003/0026848 A1 | 2/2003 | Joshi |
| 2003/0035825 A1 | 2/2003 | Shiau et al. |
| 2003/0059484 A1 | 3/2003 | Bonte et al. |
| 2003/0068351 A1 | 4/2003 | Roig |
| 2003/0072819 A1 | 4/2003 | Tao |
| 2003/0077304 A1 | 4/2003 | McCadden |
| 2003/0077332 A1 | 4/2003 | Godfrey |
| 2003/0082219 A1 | 5/2003 | Warren et al. |
| 2003/0082223 A1 | 5/2003 | Healy et al. |
| 2003/0099721 A1 | 5/2003 | Yoshida et al. |
| 2003/0118623 A1 | 6/2003 | De Paoli Ambrosi |
| 2003/0133991 A1 | 7/2003 | Monroe et al. |
| 2003/0138497 A1 | 7/2003 | Sakuma et al. |
| 2003/0161892 A1 | 8/2003 | McFarland |
| 2003/0190371 A1 | 10/2003 | Graaf et al. |
| 2003/0194446 A1 | 10/2003 | Akes et al. |
| 2003/0199488 A1 | 10/2003 | Trotta |
| 2003/0215412 A1 | 11/2003 | Waugh et al. |
| 2003/0215522 A1 | 11/2003 | Johnson et al. |
| 2003/0224023 A1 | 12/2003 | Faryniarz et al. |
| 2003/0224027 A1 | 12/2003 | Faryniarz et al. |
| 2004/0022863 A1 | 2/2004 | Hamtini |
| 2004/0028708 A1 | 2/2004 | Brooks |
| 2004/0033270 A1 | 2/2004 | Kropf et al. |
| 2004/0037910 A1 | 2/2004 | Hon et al. |
| 2004/0052741 A1 | 3/2004 | Wortzman et al. |
| 2004/0058011 A1 | 3/2004 | Petersson |
| 2004/0058015 A1 | 3/2004 | Tao |
| 2004/0062730 A1 | 4/2004 | Kurosawa et al. |
| 2004/0062817 A1 | 4/2004 | Peshoff |
| 2004/0076686 A1 | 4/2004 | Riesinger |
| 2004/0091551 A1 | 5/2004 | Damji |
| 2004/0101541 A1 | 5/2004 | Heffernan et al. |
| 2004/0109902 A1 | 6/2004 | McDonagh et al. |
| 2004/0131700 A1 | 7/2004 | Cifra et al. |
| 2004/0147189 A1 | 7/2004 | Smith et al. |
| 2004/0156875 A1 | 8/2004 | Fabre et al. |
| 2004/0157921 A1 | 8/2004 | Cifra et al. |
| 2004/0170701 A1 | 9/2004 | Carter |
| 2004/0170703 A1 | 9/2004 | Hoekstra et al. |
| 2004/0170712 A1 | 9/2004 | Sadek El Mogy |
| 2004/0175433 A1 | 9/2004 | Thomson |
| 2004/0185015 A1 | 9/2004 | Zhang et al. |
| 2004/0185016 A1 | 9/2004 | Popp et al. |
| 2004/0185074 A1 | 9/2004 | Faryniarz et al. |
| 2004/0202689 A1 | 10/2004 | Subramanyan et al. |
| 2004/0220100 A1 | 11/2004 | Waugh et al. |
| 2004/0253321 A1 | 12/2004 | Fechner et al. |
| 2004/0258769 A1 | 12/2004 | Barker et al. |
| 2005/0048010 A1 | 3/2005 | Klis et al. |
| 2005/0069506 A1 | 3/2005 | Katusic et al. |
| 2005/0069588 A1 | 3/2005 | Taal |
| 2005/0074425 A1 | 4/2005 | Waugh et al. |
| 2005/0079229 A1 | 4/2005 | Cawthon |
| 2005/0100571 A1 | 5/2005 | Keyes |
| 2005/0123620 A1 | 6/2005 | Chiou |
| 2005/0125014 A1 | 6/2005 | Duluco et al. |
| 2005/0136129 A1 | 6/2005 | Verheul-Koot et al. |
| 2005/0175719 A1 | 8/2005 | Sun et al. |
| 2005/0202054 A1 | 9/2005 | Faryniarz et al. |
| 2005/0234239 A1 | 10/2005 | Taillefer et al. |
| 2005/0238730 A1 | 10/2005 | Le Fur et al. |
| 2006/0029682 A1 | 2/2006 | Monroe et al. |
| 2006/0036007 A1 | 2/2006 | Hsieh et al. |
| 2007/0184017 A1 | 8/2007 | Faryniarz et al. |
| 2007/0191620 A1 | 8/2007 | Ramirez et al. |
| 2007/0203354 A1 | 8/2007 | Ramirez et al. |
| 2008/0081077 A1 | 4/2008 | Faryniarz et al. |
| 2010/0144870 A1 | 6/2010 | Ramirez et al. |

FOREIGN PATENT DOCUMENTS

| | | |
|---|---|---|
| WO | WO 94/15216 | 7/1994 |
| WO | WO 01/85102 A2 | 11/2001 |
| WO | WO 2004/039238 A2 | 5/2004 |

OTHER PUBLICATIONS

Nabeshima et al, Tetrahedron, 2007, 63, 3328-3333.*
Sason et al, Langmuir, 2012, 28(8), 3773-3782.*
Rodríguez-Martíin Y., "Alternating cationic-anionic layers in the [MII($H_2O)_6$][$Cu^{II}$(mal)$_2$($H_2O$)] complexes linked through hydrogen bonds (M = Mn, Co, Ni, Cu and Zn; $H_2$mal = Malonic acid)", CrystEngComm, 2002, vol. 4, No. 107, 631.
Hernández-Molina M., "A phase transition in the novel three-dimensional compound [$Eu_2$(mal)$_2$($H_2O)_6$] ($H_2$mal = malonic acid)", J.Chem.Soc., Dalton Trans. 2002, vol. 18, 3462.
Rodríguez-Martín, Y., "Structural Versatility of the Malonate Ligand as a Tool for Crystal Engineering in the Design of Molecular Magnets", Cryst. Eng. Comm. 2002, vol. 4, No. 87, 522-535.
Sanchiz, J., "Ferromagnetic coupling in the malonato-bridged copper(II) chains {[Cu(Im)$_2$(mal)]}$_n$ and {[Cu(2-MeIm)$_2$(mal)]}$_n$ (H2mal = Malonic Acid, Im = imidazole and 2-MeIm = 2-methylimidazole)", New J. Chem. 2002, vol. 26, 1624.
Rodríguez-Martín, Y., "The flexibility of molecular components as a suitable tool in designing extended magnetic systems", Cryst. Eng. Comm. 2002, vol. 4, No. 73, 440-446.
Ruiz-Pérez, C., "Dimensionally controlled hydrogen-bonded nanostructures: Synthesis, structure, thermal and magnetic behaviour of the tris-(chelated)nickel(II) complex [Ni(bipy)$_3$]$C1_2$.5.5$H_2O$ (bipy = 2,2'-bipyridine)", Inorg. Chim. Acta. 2002, vol. 336, 131-136.
Rodríguez-Martín, Y., "Extended network via hydrogen bond linkages of coordination compounds: Synthesis, crystal structure and thermal behavior of the complexes [MII(L)$_2$(NO$_3$)$_2$] (MII = Cu, Co) and [Ni(L)$_2$($H_2O$)$_2$]•(NO$_3$)$_2$ (L = malonamide)", Inorganica Chimica Acta . vol. 328, 169-178 (2002).
Rodríguez-Martín, Y., "Synthesis, crystal structure and magnetic properties of [Cu(bPYm)(inal)($H_2O$)]•and [$Cu_2$(bpym)(mal)$_2$($H_2O$)$_2$]•4$H_2O$ (bpym = 2,2'-bipyrimidine, H2mal = Malonic Acid)", Inorganica Chimica Acta. vol. 326, 20-26 (2001).
Delgado, F., "Alkali-Templated Malonate Copper (II) Complexes", Acta Cryst. A61, C358 (2005).
Naumov, P, et al., "The Crystal Structure of Copper (II) Malonate Trihydrate", CCACAA, vol. 75, No. 3, 701-711 (2002).
Filippova I.G., "Polymorphism of Coordination Compounds with Malonic Añid", Moldavian Journal of the Physical Sciences, 1vol. 1, No. 3, 87-93 (2002).
Tinker, D. et al., "Role of Selected Nutrients in Synthesis, Accumulation, and Chemical Modification of Connective Tissue Proteins", Physiolgical Reviews, vol. 65, No. 3, 607-657 (1985).
Philip, B., et al., "Dietary Zinc & Levels of Collagen, Elastin & Carbohydrate Components of Glycoproteins of Aorta, Skin & Cartilage in Rats", Indian J. Exp. Biol., vol. 16, 370-372 (1978).
Homsy, R. et al., "Characterization of Human Skin Fibroblasts Elastase Activity", J. Invest. Dermatol, vol. 91, 472-477 (1988).
1995 U.S. Pharmacopceia/National Formulary USP 23/NF 18, pp. 769-770 and 1572-1573.
Tina S. Alster, "Combined Laser Resurfacing and Tretinoin Treatment of Facial Rhytides", Cosmetic Dermatology, vol. 10, No. 11, pp. 39-42 (Nov. 1997).
Nicholas Lowe, "Understanding How Topical Retinoids Work", Skin & Aging, pp. 39-42 (Feb. 1999).
Olsen, et al. "Tretinoin Emollient Cream for Photodamaged Skin: Results of 48-Week, Multicenter, Double-Blind Studies", Journal of the American Academy of Dermatology, pp. 217-226 (Aug. 1997).
Green, et al. "Photoaging and the Skin", Dermatologic Clinics, vol. 11, No. 1 pp. 97-105 (Jan. 1993).
Buka et al. "How to use Retinoids to Prevent Skin Cancer and Treat Photoaging", Skin & Aging, pp. 32-39 (Jun. 1999).
Brochure—The Science of Skin Health Restoration—Nu-Derm System (2000).
Photo of Obagi Nu-Derm™ Toner I™, back image (1997).
Photo of Obagi Nu-Derm™ Toner II™, front and back images (1995).
Photo of Obagi Nu-Derm™ Cleanser II™, front and back images (1997).
Photo of Obagi Nu-Derm™ Clear™, front and back image (1997).
Photo of Obagi Nu-Derm™ Exfoderm™, front and back image (1997).
Photo of Obagi Nu-Derm™ Action™, front and back image (1999).
Insert, Obagi Medical Products, Inc., Long Beach, CA 90502 (2000).

Chen et al., "Preparation and Kinetics of the Thermal Decomposition of Nanosized $CuC_2O_4$-$ZnC_2O_4$ $2H_2O$", Wuhan University Journal of Natural Sciences, vol. 11, No. 3, pp. 667-671, May 2006.

M.A. Gabal, "Kinetics of the Thermal Decomposition of $CuC_2O_4$-$ZnC_2O_4$ Mixture in Air", Thermochimica Acta 402 (2003) pp. 199-208.

Huang Lianrong et al., "Thermal Behavior of Kinetics of the Decomposition of $CuC_2O_4$-$ZnC_2O_4$ $2H_2O$ by Different Preparation Methods", Journal of South-Central University for Nationalities (Nat. Sci. Edition), vol. 23, No. 3, pp. 12-16, Sep. 2004.

* cited by examiner

COMPOSITIONS, KITS AND REGIMENS FOR THE TREATMENT OF SKIN, ESPECIALLY DÉCOLLETAGE

RELATED APPLICATIONS

The present application claims priority to U.S. Provisional Application No. 61/019,047 filed on Jan. 4, 2008.

TECHNICAL FIELD

The present disclosure relates to compositions, kits and methods for treating skin, especially décolletage. The method includes the application of a retinoid, hydroquinone or a hydroquinone derivative and a composition containing a multi-metal complex.

BACKGROUND

The problems associated with the complexion of décolletage are less frequently given attention, as compared with e.g. the face. With advancing age, however, wrinkles and pigmented spots can appear on the décolletage. One approach that has been used in an attempt to reduce the signs of aging of the décolletage is therapy with laser. In theory, exposure to the laser rays helps the collagen in the skin partly recover; with some old and damaged collagen filaments being absorbed and in about six weeks a new skin skeleton is established, with new collagen that is more flexible. Pigmented spots, typical in the décolletage, may likewise be removed by laser. Essentially, the laser energy passes through the surface of skin and disintegrates the pigment into minute fragments that are absorbed by the body after a short time. Another approach to reduce wrinkles in the décolletage is by injecting the filling materials. Each of these treatments requires application by a professional.

It would be desirable to provide a regimen for treatment of the décolletage which is effective in reducing wrinkles, lightening age spots, is well tolerated by the skin and can be administered by the user without professional supervision.

SUMMARY

Regimens for treatment of damaged skin, especially décolletage, are described which include application of a retinoid, hydroquinone and a composition containing a multi-metal complex. The retinoid can be tretinoin. The multi-metal complex contained is a compound having at least two different metal cations in the same molecule and can be the reaction product of a polyfunctional acid with two or more coordination elements.

In embodiments, the composition containing a multi-metal complex includes at least one compound of a multifunctional carboxylic acid having copper and zinc cations in the same molecule which can be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

In embodiments, hydroquinone and retinoid are applied as individual compositions. In other embodiments, hydroquinone and retinoid are applied as a single composition prepared by combining a hydroquinone-containing blending composition with a retinoid immediately prior to application to the skin as a pre-mixed composition. One particularly useful blending composition contains hydroquinone (40 mg/gm) (drug ingredient) in a base of water, glycerin, cetyl alcohol, PPG-2 myristyl ether propionate, sodium lauryl sulfate, TEA-salicylate, lactic acid, phenyl trimethicone, tocopheryl acetate, sodium metabisulfite, ascorbic acid, methylparaben, saponins, disodium EDTA, BHT and propylparaben.

In embodiments, the regimen includes morning and evening applications, with the morning application including the sequential application of the hydroquinone-containing blending composition and a composition containing a multi-metal complex and optionally a sun protecting composition and the evening application including the sequential application of a first composition prepared by mixing a retinoid with a hydroquinone-containing blending composition and a second composition containing a multi-metal complex.

The retinoid, hydroquinone, and composition containing a multi-metal complex may be packaged together in a kit. In embodiments, the kit may contain the multi-metal complex, the retinoid, and the hydroquinone each contained in separate containers. In other embodiments, the kit may include a first container containing the composition containing a multi-metal complex, a second container containing a hydroquinone-containing blending composition, and a third container containing a retinoid formulated for mixing with the blending composition.

DETAILED DESCRIPTION OF PREFERRED EMBODIMENTS

Compositions, kits and regimens for treatment of skin, especially the décolletage, in accordance with the present disclosure include a retinoid, hydroquinone and a multi-metal complex and their application to a non-facial area of the skin of a user.

The Multi-Metal Complex-Containing Composition

The composition containing a multi-metal complex include a topically acceptable carrier and at least one multi-metal complex. The multi-metal complex is the reaction product of a polyfunctional compound (in embodiments a polyfunctional acid or an amino acid) with two or more different coordination elements resulting in a compound having at least two different metal cations in the same molecule.

The polyfunctional acid can be any compound that contains at least two acid groups that may complex with metal cations in solution. The at least two acid groups may be organic or inorganic acids, such as, for example, two carboxylic acid groups or at least two phosphoric acid groups. Polyfunctional acids are primarily monomeric compositions having two or more carboxylic acid groups. Non-limiting examples of polyfunctional acids include maleic acid, fumaric acid, citric acid, citraconic acid, itaconic acid, glutaconic acid, phthalic acid, isophthalic acid, terephthalic acid, cyclohexane dicarboxylic acid, succinic acid, adipic acid, sebacic acid, azealic acid, malonic acid, dodecanedioic acid, 1,18-octadecanedioic acid, dimer acids (prepared from a mono-, di- or triunsaturated fatty acid, acid wax, acid anhydride grafted wax, or other suitable polycarboxylic acid reacting compound), alkenyl succinic acids (such as n-dodecenyl-succinic acid, docecylcucinic acid and octadecenylsuccinic acid), azaleic acid, phytic acid and the like. The polyfunctional acid can be present in acidic form, anhydride form, partially neutralized salt forms, or mixtures thereof.

The polyfunctional acid is reacted with two or more coordination elements. The coordination elements can be chosen from the elements listed in Groups IIIA to VIIIA, Groups IB to IIIB, of periods 4 and 5 and aluminum in Group IIIB, period 3 of The Periodic Table of the Elements. Suitable non-limiting examples of elements listed in group IB of The Periodic Table of Elements include copper and silver. Suitable non-limiting examples of coordination elements include aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium. Tin may also be used. Those skilled in the art will readily envision suitable compounds for providing the coordination elements in the reaction mixture.

Non-limiting examples of compounds that may be used to provide coordination elements in the reaction mixture can include free metals, ammonium compounds, carbonates, hydroxides and oxide compounds of the coordination elements. Suitable copper compounds include copper, copper hydroxide, copper borate, copper carbonate and copper oxide. Suitable zinc compounds include zinc metal, zinc oxide, zinc borate, zinc metaborate, basic zinc borate, zinc glycerophosphate, zinc citrate, zinc picrate and zinc hydrogen phosphate. It should be understood that the listed compounds are only a small portion of the compounds suitable for use in accordance with the present disclosure. For example, inorganic compounds are suitable provided that they provide coordination element cations when placed in an aqueous solution with the polyfunctional compound. Thus, the foregoing list of compounds should be considered a non-limiting, illustrative list.

For carrying out the process, a reaction solution can be prepared by mixing the various ingredients in water. Water in the mixture may advantageously be added in limited amounts sufficient to allow the reaction product to precipitate from solution upon formation. Where necessary, mixing and heating can be used to bring the reactants to 40-100° C. in order to solubilize the reactants and start reactions. As a result, reactant solubility may be enhanced through energy input such as microwave heating or addition of boiling water. The input of the energy may take place through any instrument capable of heating the aqueous reaction mixture. The reaction products formed in solution may be immediately separated so that their production can take place in a continuous process. Where a short reaction time and rapid crystallization of the reaction product occur, the conversion may be carried out continuously, and the recovery of the resultant solid product may take place by any conventional manner such as filtering, centrifugation, or sedimentation.

The polyfunctional acid is present in the reaction mixture in amounts that will contact metal cations in an aqueous solution. Suitable amounts of polyfunctional acid also include excess amounts in relation to the amount of metal cations. In embodiments, polyfunctional acid is present in a 3:1:1 molar ratio in relation to the metal constituents. In embodiments, the polyfunctional acid is malonic acid which can be present in acidic form, partial salt form, or mixtures thereof.

In embodiments, the process parameters are especially advantageous if the polyfunctional acid is added to excess in comparison to the metal counter cation constituents. Depending on the desired complex, the latter are added so that the molar ratio of polyfunctional acid to metal ions is approximately 3:2.

In embodiments, the coordination elements may be present as one or more ionic compounds formed by joining one or more independent coordination element molecules or ions of a first type and coordination element molecules or ions of a second type to a central unit by ionic bonds. For example, the reaction product may be in the form of a trinuclear cation, where structurally independent coordination element hydrates are bridged by a central unit. However, various coordination modes are possible depending on the source of the coordination elements and synthesis conditions. In embodiments, the central unit may be a multi-membered ring such as eight-membered ring, six-membered ring, and four-membered metalocycle for bridging or chelating functions between the coordination element constituents. Accordingly, the crystal structures of the reaction products can be very diverse, from ionic to three-dimensional polymers. In embodiments, the reaction products are present in several hydrate, and polymorphic forms.

In embodiments, suitable reaction products can be non-toxic multi-metal complexes that include copper, zinc, aluminum and/or silver constituents. Such copper, zinc, aluminum and/or silver reaction products include, but are not limited to compounds that contain copper, zinc, aluminum and/or silver. Non-limiting examples of bimetal complexes include copper-zinc citrate, copper-silver citrate, silver-zinc citrate, copper-zinc oxalate, copper-silver oxalate, silver-zinc oxalate, copper-zinc tartarate, copper-silver tartarate, silver-zinc tartarate, copper-zinc malate, copper-silver malate, silver-zinc malate, copper-zinc succinate, copper-silver succinate, silver-zinc succinate, copper-zinc malonate, copper-silver malonate, silver-zinc malonate, copper-zinc maleate, copper-silver maleate, silver-zinc maleate, copper-zinc aspartate, copper-silver aspartate, silver-zinc aspartate, copper-zinc glutamate, copper-silver glutamate, silver-zinc glutamate, copper-zinc glutarate, copper-silver glutarate, silver-zinc glutarate, copper-zinc fumarate, copper-silver fumarate, silver-zinc fumarate, copper-zinc glucarate, copper-silver glucarate, silver-zinc glucarate, copper-zinc polyacrylic acid, copper-silver polyacrylic acid, silver-zinc polyacrylic acid, and combinations thereof. In embodiments, copper, zinc, aluminum and silver salts of organic multi carboxylic acids are suitable for use in accordance with the present disclosure. In embodiments, suitable compounds can be doped such that the unit cell of the coordination compound has zinc or silver constituents dispersed therein. Such zinc or silver constituents may either substitute another metallic constituent or fill a preexisting void in the unit cell.

In embodiments, suitable reaction products can be copper compounds having zinc or silver constituents therein. For example, zinc or silver may either substitute a copper constituent or fill a preexisting void in the copper compound's unit cell. Suitable non-limiting examples of copper compounds which may be used to form multi-metallic complexes include copper (II) malonate and any hydrated form thereof such as copper (II) malonate dihydrate, copper (II) malonate trihydrate, and copper malonate tetrahydrate. Other suitable non-limiting examples of suitable copper active ingredients include copper citrate, copper oxalate, copper tartarate, copper malate, copper succinate, copper malonate, copper maleate, copper aspartate, copper glutamate, copper glutarate, copper fumarate, copper glucarate, copper polyacrylic acid, and combinations thereof. In embodiments, suitable copper compounds can be doped such that the unit cell of the compound has zinc or silver constituents dispersed therein. Such zinc or silver constituents may either substitute a copper constituent or fill a preexisting void in the unit cell.

In embodiments, the compositions may contain any active ingredient or be formulated and applied as described in commonly owned U.S. patent application entitled Anti-aging Treatment Using Copper-Zinc Compositions (U.S. Ser. No. 11/452,642 filed Jun. 14, 2006) herein incorporated by reference in its entirety. Amino acids may also be used as the polyfunctional compound. Amino acids are known to those skilled in the art and include those containing at least a dicarboxylic acid functionality and an amino functionality. Suitable amino acids include naturally occurring amino acids and synthetic amino acids. Non-limiting examples of amino acids include, but are not limited to: aminopolycarboxylic acids (e.g., aspartic acid, β-hydroxyaspartic acid, glutamic acid, β-hydroxyglutamic acid, β-methylaspartic acid, β-methylglutamic acid. Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid. Polyaminoacids may also be used provided they form complexes with the coordination elements employed.

Cu/Zn Malonate Embodiments

In embodiments, malonic acid may be reacted with compounds containing copper and zinc constituents in an aqueous solution. It has been found that where the malonic acid, copper and zinc constituents are present in at least about a 3:1:1 molar ratio, copper-zinc malonates may be produced in good yield and high crystalline purity.

Malonic acid refers to 1,3-propanedioic acid, a dicarboxylic acid with structure $CH_2(COOH)_2$ or:

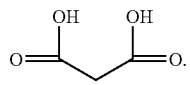

The ion form of malonic acid, as well as its esters and salts, are known as malonates. For example, diethyl malonate is ethyl ester of malonic acid. As used herein, the term copper-zinc malonate applies to any salt substances formed from malonic acid having copper and zinc constituents.

Suitable ingredients for the formation of copper-zinc malonates include malonic acid, one or more bases of copper and zinc, and water. In an aqueous reaction solution, suitable salt forms provide copper and zinc cations capable of bonding to malonate anions. Other suitable ingredients for the formation of copper-zinc malonates will include the replacement of bases of copper and zinc with the metallic form of copper and zinc. The elemental form of copper and zinc are known as copper and zinc metals and will be dissolved in the acidic water media as they react with malonic acid.

One or more compounds containing copper and zinc constituents are present in amounts that will contact malonic acid in an aqueous solution. Suitable compounds for making copper-zinc malonate compositions in accordance with this disclosure include compounds containing complex-forming metal ions of copper and/or zinc. In embodiments, the aqueous solution may include one or more metallic compounds, such as cupric carbonate ($CuCO_3.Cu(OH)_2$), zinc carbonate ($3Zn(OH)_2.2ZnCO_3$), metallic copper, metallic zinc and combinations thereof. Basic compounds such as basic zinc compounds, basic copper compounds, and combinations thereof are also suitable for use in accordance with the present disclosure. In embodiments, suitable metal basic compounds are: copper (I) and (II) compounds such as copper carbonate, copper oxide, and copper hydroxide; and zinc compounds such as zinc carbonate, zinc oxide, and zinc hydroxide.

It should be understood that the listed compounds are only a small portion of the compounds suitable for use in accordance with the present disclosure. For example, inorganic compounds are suitable provided that they provide copper and zinc cations when placed in an aqueous solution with the polyfunctional compound. Thus, the foregoing list of compounds should be considered a non-limiting, illustrative list.

For carrying out the process, the reaction solution can be prepared by mixing the various ingredients in water where malonic acid and the coordination element providing compounds may ionize and become more reactive. Water in the mixture is added in amounts sufficient to allow copper-zinc malonates to form. Where copper and zinc compounds in the reaction mixture are insoluble and form dispersions (such as at cooler temperatures), mixing and heating steps can be applied to bring the reactants to 40-100° C. in order to solubilize the reactants and start reactions. As a result, reaction rates may be enhanced through energy input such as microwave heating or addition of boiling water dissolver. The input of the energy may take place through any instrument capable of heating the aqueous reaction mixture. The copper-zinc malonate complexes formed in solution may be immediately separated so that their production can take place in a continuous process. Due to the short reaction time and the rapid crystallization of the copper-zinc malonate product, the conversion may be carried out continuously, and the recovery of the resultant solid product may take place by any conventional manner such as filtering, centrifugation, or sedimentation.

In the production of the reaction mixture, the concentration of the polyfunctional compound and that of the copper and zinc constituents may be pre-selected so that the total concentration of product formed exceeds the solubility equilibrium. This will result in product precipitating from solution in solid form for easy collection.

In embodiments, the final composition may be a deep blue crystal having good yield and substantial crystalline purity. Suitable copper-zinc malonate forms in accordance with the present disclosure include any salt formed from the neutralization of malonic acid by one or more copper containing molecules and one or more zinc containing molecules. Illustrative examples include salt formed by the neutralization of malonic acid by cupric carbonate ($CuCO_3.Cu(OH)_2$), and zinc carbonate ($3Zn(OH)_2.2ZnCO_3$) in an aqueous solution. Here zinc may be added first, followed by copper in order to obtain the salts of the present disclosure.

In embodiments, the copper-zinc malonates may be one or more ionic compounds formed by joining one or more independent copper molecules or ions and one or more independent zinc molecules or ions to a central unit by ionic bonds. For example, the copper-zinc malonate may be in the form of a trinuclear cation, where structurally independent copper and zinc hydrates are bridged by a central unit such as an octahedral diaquadimalonatocopper (II) unit. However, various coordination modes are possible depending on the source of the copper and zinc and synthesis conditions. In embodiments, the central unit malonate ion may be a multi-membered ring such as eight-membered ring, six-membered ring, and four-membered metalocycle for bridging or chelating functions between the copper and zinc constituents. Accordingly, the crystal structures of copper-zinc malonates can be very diverse, from ionic to three-dimensional polymers. In embodiments, the copper-zinc malonates can be found in several hydrate, and polymorphic forms.

In embodiments, the process parameters are especially advantageous if the polyfunctional compound is added to excess in comparison to the metal counter cation constituents.

Depending on the desired complex, the latter are added so that the molar ratio of polyfunctional compound to metal ions is approximately 3:2.

Formulations Containing the Multi-Metallic Complex

The resulting compounds having at least two metal cations in the same molecule serve as active ingredients in the multi-metal complex-containing composition used in the presently described regimens for treatment of skin. Such active ingredients may be combined with numerous ingredients to form products of numerous chemical applications, such as catalytical agents, crosslinking of polymers, superconducting electrical materials, pharmaceutical drugs, food supplements, etc. The active ingredients in suitable compositions can be topically applied to the skin, or into other tissues of humans or other mammals. Such products may include a dermatologically or pharmaceutically acceptable carrier, vehicle or medium, for example, a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. In embodiments, compositions in accordance with the present disclosure can contain any ingredient conventionally used in cosmetics and/or dermatology. In embodiments, active ingredients may be formulated to provide crystals in solution, as well as solid forms.

In embodiments, products containing a reaction product in accordance with the present disclosure as an active ingredient can be in the form of solutions, emulsions (including microemulsions), suspensions, creams, lotions, gels, powders, or other typical solid or liquid compositions used for treatment of damaged skin. Such compositions may contain, in addition to the reaction product in accordance with this disclosure, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

As an illustrative example, products can be formulated to contain multi-metal complexes in amounts from about 0.001 to about 5% by weight of the total composition. In embodiments, products can be formulated to contain multi-metal complexes in an amount from about 0.05 to about 1.0% by weight of the total composition. In other embodiments, the amount of multi-metal complexes is from about 0.1 to about 0.5% by weight of the total composition. Here, the multi-metal complexes present may be in a pharmaceutically acceptable salt form. Other active ingredients may be provided in the formulations at the same concentrations.

Table 2 below provides illustrative emulsion formulations suitable for the composition containing one or more multi-metal complexes.

TABLE 2

| Phase | Ingredient | Illustrative compound(s) | Suitable range |
| --- | --- | --- | --- |
| Water Phase | Solvent | Water<br>Polyalkylene glycol | from about 50% to about 80% by weight of the emulsion composition |
| Water Phase | Humectant | Glycerine<br>Polyalkylene glycol | from about 0.05% to about 10% by weight of the emulsion composition |
| Water Phase | Preservative | Phenoxyethanol<br>Methylparaben<br>Ethylparaben | from about 0.01% to about 5.0% by weight of the emulsion composition |
| Water Phase | Emollient | Dipropylene glycol | from about 0.01% to about 10% by weight of the emulsion composition |
| Water Phase | Buffer | NaOH solution | from about 0.01% to about 10% by weight of the emulsion composition |
| Oil Phase | Solvent | isohexadecane | from about 5% to about 20% by weight of the emulsion composition |
| Oil Phase | Emollient | Isohexadecane<br>Coco-caprylate/caprate<br>$C_{13}$-$C_{15}$ alkane<br>Ethylhexyl palmitate | from about 2% to about 20% by weight of the emulsion composition |
| Oil Phase | Emulsifier | Glyceryl Stearate<br>Polyalkelene glycol stearate | from about 0.1% to about 5% by weight of the emulsion composition |

TABLE 2-continued

| Phase | Ingredient | Illustrative compound(s) | Suitable range |
|---|---|---|---|
| Oil Phase | Thickener | Cetyl alcohol<br>Stearyl alcohol<br>Simulgel NS* | from about 1% to about 10% by weight of the emulsion composition |
| Oil Phase | Preservative | Propylparaben<br>Butylparaben | from about 0.01% to about 5% by weight of the emulsion composition |
| Oil Phase | Miscellaneous** | Blueberry extract<br>Mica<br>Titanium dioxide<br>Iron oxide<br>Talc<br>Alumina<br>Silica | from about 0.0001% to about 5% by weight of the emulsion composition |

*Commercially available from Seppic Corporation, Fairfield, N.J..

**May be present as Flamenco Satin Green P860, commercially available from Engelhard Corporation, Iselin, NJ; Kobo BPD 500 commercially available from Kobo Products, South Plainfield, NJ and/or Cloverleaf AR - 80 commercially available from Presperse Inc. Somerset, NJ.

Retinoid Compositions

Prior to application of the composition containing a multi-metal complex, the skin is treated in accordance with the present regimens by application of both a retinoid and hydroquinone. The retinoid may be applied as a composition containing a retinoid and a dermatologically or pharmaceutically acceptable carrier.

Non-limiting examples of suitable retinoids include isotretinoin, retinal, retinol, retinoic acid, retinyl acetate, retinyl palmitate, retinyl propionate, synthetic retinoid mimics, and tretinoin. In embodiments, the retinoid is tretinoin. The retinoid may be present in the composition in an amount ranging from about 0.005% to about 1.0% by weight of the composition. In one embodiment, for example, the retinoid is present in an amount ranging from about 0.025% to about 0.75% by weight. In another embodiment, the retinoid is present in an amount of about 0.50% by weight. The retinoid may be formulated into a composition suitable for topical application using conventional ingredients formulated using techniques within the purview of those skilled in the art.

Suitable retinoid compositions for use as the second composition are commercially available and include, but are not limited to RETIN-A MICRO® (Commercially available from Orthoneutrogena, Skillman, N.J.), RENOVA® (Commercially available from Orthoneutrogena, Skillman, N.J.), AVAGE® (Commercially available from Allergan, Inc., Irvine, Calif.), TAZARAC® (Commercially available from Allergan, Inc., Irvine, Calif.), TAZAROTENE® (Commercially available from Allergan, Inc., Irvine, Calif.), ADAPALENE® (Commercially available from Galderma Laboratories, LP, Fort Worth, Tex.), DIFFERIN® (Commercially available from Galderma Laboratories, LP, Fort Worth, Tex.), AVITA® (Commercially available from Renederm Inc., Foster City Calif.), AFFIRM® (Commercially available from CosMedix, LLC, Atlanta, Ga.).

In accordance with the present regimens, hydroquinone is also applied to the skin prior to application of the composition containing the multi-metal complex. Hydroquinone can be applied before, after or simultaneously with the retinoid.

The hydroquinone compositions of the present disclosure contain hydroquinone or a hydroquinone derivative and a dermatologically or pharmaceutically acceptable carrier. Hydroquinone is a well-known compound having the general formula:

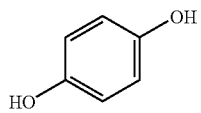

The hydroquinone is present in amounts that provide a benefit to the skin of a user. In embodiments, hydroquinone is present in an amount sufficient to effect depigmentation. Generally, hydroquinone in amounts from about 0.1 to about 10% by weight of the total composition is suitable. In embodiments, hydroquinone is present in an amount from about 1 to about 5% by weight of the total composition. In yet other embodiments, hydroquinone is present in an amount from about 2.5 to about 4.5% by weight of the total composition.

Suitable hydroquinone compositions for use as in the present treatment regimens include, but are not limited to commercially available products such as, for example GLYTONE® Fading Lotion (2% HQ), MELA-D® by La Roche-Posay, ESSENTIAL SKIN LIGHTENER® by Exuviance, PIGMENT GEL—Phaze 13 by PCA Skin®, 6% SKIN BLEACHING CREAM by Physician's Complex, CONDITIONING GEL PLUS by Biomedic, PIGMENTAION FADER by pH Advantage, LUMEDIA by Lumedia, POTENT SKIN LIGHTENING GEL COMPLEX by Peter Thomas Roth, HQ SKIN LIGHTENING GEL PHA by NeoStrata, SKIN LIGHTENING TREATMENT by B. Kamins, In the context of the present disclosure, the term "hydroquinone derivative" is understood to mean compounds that are substituted hydroquinones wherein the substitution does not significantly affect one or more of the enzyme inhibition function of hydroquinone, the melanocidal activity of hydroquinone or the reducing capacity of the hydroquinone. The hydroquinone derivatives have the formula:

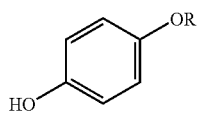

wherein R is a group that maintains the skin lightening functionality of hydroquinone and results in a non-toxic compound suitable for topical application to the skin of a user.

In embodiments, the R group results in the production of a glycoside of hydroquinone. In such embodiments R represents a pentose residue, a hexose residue, an amino sugar residue, or a uronic acid residue, or the methylated product thereof in a skin treatment base. Techniques for the preparation of such compounds are disclosed in U.S. Pat. No. 5,310,730, the entire contents of which are incorporated herein by this reference. Arbutin is an example of one suitable glycoside of hydroquinone.

Other examples of suitable substituted hydroquinones include monoalkyl ethers and hydroquinone monoaryl ethers. Such hydroquinone ethers are described in Japanese Patent Applications Nos. JP-06 192 062 and JP-61 159 943; ethers of hydroquinone and of a heterocyclic alcohol, as described in U.S. Pat. No. 6,139,854, which is also incorporated in its entirety herein by reference; (2,5-dihydroxyphenyl) carboxylic acid derivatives described, for example, in application U.S. Pat. No. 5,449,518, which is also incorporated in its entirety herein by reference; hydroquinone which is substituted, in particular, with alkylthio or alkoxy groups.

Non-limiting examples of hydroquinone derivatives include: 2,5-dihydroxyphenyl propionic acid, the ethyl ester of 2,5-dihydroxyphenyl propionic acid; the lauryl ester of 2,5-dihydroxyphenylpropionic acid; methyl 2,5-dihydroxy-3,4-dimethylphenyl acetate; 2,5-dihydroxy-4-methylphenyl acetic acid; alkyl esters of 2,5-dihydroxy-4-methylphenyl acetic acid; 2,5-dihydroxy-4-methylphenyl propionic acid; ethyl ester of 2,5-dihydroxy-4-phenylpropionic acid; 2,5-dihydroxy-4-methylbenzoic acid; methyl ester of 2,5-dihydroxy-4-methylbenzoic acid; ethyl ester of 2,5-dihydroxy-4-methylbenzoic acid; 2,5-dihydroxy-4-ethylbenzoic acid; 2,5-dihydroxy-4-methoxybenzoic acid; methyl ester of 2,5-dihydroxy-4-methoxybenzoic acid; 2,5-dihydroxy-4-ethoxybenzoic acid; 3-(2,5-dihydroxy-4'-methylphenyl)-1-N-(.omega.-carboxydecyl)propylamide; 2,5-dihydroxy-4-methylphenylbutanoic acid; 2,5-dihydroxy-4-methylpenylhexanoic acid; 2,5-dihydroxy-4-methoxyphenylacetic acid; methyl ester of 2,5-dihydroxy-4-methoxyphenylacetic acid; 2,5-dihydroxy-4-methoxybenzylamide; methyl 2,5-dihydroxy-3-methoxyphenylacetate 2,5-dihydroxy-3-methoxyphenylpentadecylic acid; methyl ester of 2,5-dihydroxy-3-methoxyphenylpentadecylic acid; 2,5-dihydroxyphenylbutanoic acid; methyl ester of 2,5-dihydroxyphenylbutanoic acid; 2,5-dihydroxyphenylbutylamide 2,5-dihydroxyphenylpentanoic acid; 2,5-dihydroxyphenylhexanoic acid; 2,5-dihydroxyphenyloctanoic acid; 2,5-dihydroxyphenyldecylic acid; methyl ester of 2,5-dihydroxyphenyldecylic acid; 2,5-dihydroxyphenylundecylic acid; methyl ester of 2,5-dihydroxyphenylundecylic acid; 2,5-dihydroxy-3,4-dimethylphenylacetic acid; ethyl-2,5-dihydroxy-4,6-dimethylphenylacetate; 2-(2,5-dihydroxy-4-methoxyphenyl)-N-octylacetamide; 6-(2,5-dihydroxy-4-methoxyphenyl)hexanoic acid; 4-[(6-methoxy-etrahydro-2H-pyran-2-yl)oxyphenol; 4-[(tetrahydro-2H-pyran-2-yl)oxy]phenol; and 4-[(tetrahydro-2H-thiopyran-2-yl)oxy]phenol.

In embodiments, the hydroquinone derivative is selected from: 2,5-dihydroxyphenylpropionic acid; 2,5-dihydroxy-3,4-dimethylphenylacetic acid; methyl 2,5-dihydroxy-3,4-dimethylphenylacetic acid; 2,5-dihydroxy-4-methylphenylacetic acid; 2,5-dihydroxy-3,4-dimethylphenylpropionic acid; methyl 2,5-dihydroxy-4-methylphenylacetate; ethyl 2,5-dihydroxy-4-methylphenylacetate; propyl 2,5-dihydroxy-4-methylphenylacetate; isopropyl 2,5-dihydroxy-4-methylphenylacetate; butyl 2,5-dihydroxy-4-methylphenylacetate; pentyl 2,5-dihydroxy-4-methylphenylacetate; isoamyl 2,5-dihydroxy-4-methylphenylacetate; and 2-(2,5-dihydroxy-4-methylphenyl)-N-octylacetamide.

In embodiments, retinoid and hydroquinone are sequentially applied. In other embodiments, the retinoid is provided separately from and premixed with a hydroquinone-containing blending composition prior to application to the décolletage. When provided separately, the retinoid need not be formulated for topical application, but rather the blending composition may provide the necessary pharmaceutically or dermatologically acceptable carrier.

The hydroquinone-containing blending composition is designed to be blended with treinoin to be applied to the skin. A particularly useful blending composition contains an active ingredient in a base composition of water, glycerin, cetyl alcohol, PPG-2 myristyl ether propionate, sodium lauryl sulfate, TEA-salicylate, lactic acid, phenyl trimethicone, tocopheryl acetate, sodium metabisulfite, ascorbic acid, methylparaben, saponins, disodium EDTA, BHT and propylparaben. One suitable hydroquinone-containing blending composition is OBAGI NU-DERM® BLENDER® commercially available from OMP, Inc. of Long Beach, Calif.

Suitable blending compositions may also be made in accordance with the ingredients identified in Table 1.

TABLE 1

| Compound | % of total composition |
| --- | --- |
| Purified water | 70-85 |
| Preservatives | .01-1.5 |
| Chelating Agent | .01-0.5 |
| Humectants | 1-10 |
| Anionic Surfactants | .01-5 |
| Nonionic Surfactants | .01-5 |
| Organic Acid | .01-5 |
| C12-C18 Alkyl Alcohols | 2-50 |
| Antioxidants | .01-10 |
| Reducing Agents | .01-5 |
| Emollient | 1-10 |
| Hydroquinone | 0.0-10% |

Suitable preservatives for use in the blending composition further include: benzoic acid, benzyl alcohol, butylparaben, diazolidinyl urea, 2,3-Imidazolidinedione, isopropylparaben, isobutylparaben, methylparaben, propylparaben, sodium butylparaben, sorbic acid, or combinations of these preservatives.

Suitable chelating agents for use in the blending composition further include: citric acid, edetate disodium, ethylenediaminetetraacetic acid, etidronic acid sodium dihydroxyethylglycinate, nitrilotriacetic acid, and combinations of these agents.

Suitable emulsifiers for use in the blending composition further include: cetearyl alcohol, ethoxylated fatty alcohols, PEG-1000 monocetyl ether, alkyl trimethyl ammonium bromide, polyol ester glycerol monostearate, potassium stearate, sodium lauryl sulfate, sodium cetearyl sulfate, saponins, and combinations of these agents.

Suitable humectants for use in the blending composition further include: glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, panthenol, pentaerythritol, hyaluronic acid, and combinations of these humectants.

Suitable pH adjusters for use in the blending composition further include: citric acid, phosphoric acid, lactic acid, glycolic acid, and combinations of these pH adjusters.

Suitable antioxidants for use in the blending composition further include: ascorbyl palmitate, 2,6 ditertiarybutyl-4-methyl phenol, butylated hydroxyanisole, tocopherol, tocopheryl acetate, propyl gallate, and combinations of these antioxidants.

Suitable emollients for use in the blending composition further include: cetyl alcohol, stearyl alcohol, liquid hydrocarbon oil, liquid natural oil, liquid fatty alcohol, liquid fatty acid, liquid fatty acid ester, liquid silicone oil, paste wax, and combinations of these emollients.

Suitable reducing agents for use in the blending composition further include: ascorbic acid, propyl gallate, sodium metabisulfite, and combinations of these reducing agents.

Treatment Regimens

Regimens for treatment of the décolletage in accordance with the present disclosure include sequential application to the décolletage of a retinoid and hydroquinone followed by the application of the composition containing a multi-metal complex. It should, of course, be understood that the multi-metal complex may be applied before application of the retinoid and/or hydroquinone.

In embodiments the treatment regimen involves a morning application and an evening application. The morning application includes the sequential application of a retinoid and hydroquinone followed by the application of the composition containing a multi-metal complex. The evening application involves application of hydroquinone followed by the application of the composition containing a multi-metal complex. Alternatively, the morning and evening treatments can be switched, with the morning application involving application of hydroquinone followed by the application of the composition containing a multi-metal complex and the evening application including application of a retinoid and hydroquinone followed by the application of a composition containing a multi-metal complex. It should, of course, be understood that the morning and evening treatment regimens may be reversed.

In embodiments, the retinoid and hydroquinone are applied sequentially. In other embodiments, the retinoid and hydroquinone are applied as a pre-mix prepared immediately before application to the décolletage. In such embodiments, a retinoid is provided and a hydroquinone-containing blending composition is provided. The retinoid is mixed with the hydroquinone-containing blending composition immediately prior to application to the décolletage. Thus, in embodiments, the present treatment regimens include, pre-mixing a retinoid with a hydroquinone-containing blending composition, applying the pre-mixed formulation to the skin of the décolletage, and applying a composition containing a multi-metal complex to the skin of the décolletage previously treated with the pre-mixed composition.

In embodiments the treatment regimen involves a morning application and an evening application. The morning application includes, pre-mixing a retinoid with a hydroquinone-containing blending composition, applying the pre-mixed formulation to the skin of the décolletage, and application of the composition containing a multi-metal complex to the skin of the décolletage previously treated with the pre-mixed composition. The evening application involves application of the hydroquinone-containing blending composition (without retinoid) to the skin of the décolletage followed by application of the composition containing a multi-metal complex to the skin of the décolletage previously treated with the blending composition. Alternatively, the morning and evening treatments can be switched, with the morning application involving application of the hydroquinone-containing blending composition (without retinoid) to the skin of the décolletage followed by application of the composition containing a multi-metal complex to the skin of the décolletage previously treated with the blending composition and the evening application including pre-mixing a retinoid with a hydroquinone-containing blending composition, applying the pre-mixed formulation to the skin of the décolletage and the application of the composition containing a multi-metal complex to the skin of the décolletage previously treated with the pre-mixed composition. It should, of course be understood that separate retinoid and hydroquinone compositions can be applied sequentially in each of the foregoing regimens rather than forming a pre-mix composition.

Pre-packaged kits may be provided containing the products of the treatment regimen. In embodiments, the kit includes a plurality of separate containers, each containing at least one active agent useful in a combination therapy for the treatment of skin, especially décolletage. The kit contains a first container containing a retinoid, a second container containing a hydroquinone, and a third container containing a composition that includes a multi-metal complex. The containers of the kit may be enclosed within a common outer packaging, such as, for example a cardboard or plastic box or a shrink wrap outer skin enclosing the various containers. In embodiments, the retinoid, hydroquinone, and composition containing a multi-metal complex are each individually formulated in a dermatologically acceptable carrier for topical application. In other embodiments, the composition containing a multi-metal complex and the hydroquinone are formulated for topical application, and the retinoid is provided for mixing with the hydroquinone before application. In embodiments, kits contain a first set of products to be used with a first treatment regimen and a second set of products to be used with a second treatment regimen as described above.

The kits may be in the form of a consumer package or prescription package which provides the products described above. In embodiments, a combination of a consumer package with prescription product(s) may be obtained. The package may provide instructions or directions on how to use and/or combine the products for one or more treatment regimens as described above.

The regimens in accordance with this disclosure can be used to treat the décolletage or any other area of the skin. As used herein the word "treat," "treating" or "treatment" refers to using regimens of the present disclosure prophylactically to prevent outbreaks of undesirable dermatological conditions, or therapeutically to ameliorate an existing dermatological condition, and/or extend the duration of the aesthetic benefit of a skin procedure. As used herein "undesirable skin condition" refers to any skin condition that may require treatment of any sort, including skin having one or more undesirable appearances and/or disagreeable tactile sensations. The term further refers to any cosmetically undesirable skin condition, as well as any undesirable diseased or damaged skin condition.

Non-limiting examples of undesirable skin conditions which can be treated with the topical application of compositions in accordance with the present disclosure include: acne vulgaris (pimples); atopic dermatitis; birthmarks; cafe-au-laits spots; common benign skin tumors or growths; common skin conditions around the eyes such as eyelid contact dermatitis, atopic dermatitis, bacterial skin infection (impetigo or conjunctivitis), xanthelasma, syringoma, skin tags, milia, Naevus, and/or portwine stains; common skin condition associated with housework such as irritant contact dermatitis, allergic contact dermatitis, contact urticaria, fungal infections, paronychia, and/or viral warts; common diseases of the scalp such as seborrhoeic dermatitis, psoriasis of the scalp, lichen planus, discoid lupus erythematosus (DLE), alopecia greata, seborrhoeic keratoses (seborrhoeic warts, age spots), solar keratoses, angiosarcoma, fungal infection (ringworm, tinea Capitis), bacteria infections of the hair follicles (folliculitis, boils), and/or shingles (Herpes Zoster); common diseases in children such as atopic dermatitis, atopic eczema, discoid eczema, pityriasis alba, vitiligo, and/or alopecia greata; common diseases of the mouth and lips such as oral candidiasis, oral leukoplakia, apthous ulcers, and/or oral lichen planus; common skin problems in elderly such as appearance and texture changes, senile purpura, xerosis/asteatotic eczema, skin Infections/infestations, pigmentary changes, blistering disorders, non-cancerous skin growths, cancerous skin growths, adverse drug reaction, and/or stasis dermatitis; common viral warts; contact allergy; diaper candidiasis, drug allergy, folliculitis; freckles; fungal infections of the skin such as white spot, athlete's foot, jock itch, and/or moniliasis/candidiasis; guttate hypomelanosis; hair loss; hand eczema; impetigo; lines, crow's feet, wrinkles, etc.; melasma; molluscum contagiosum; occupational skin disease such as irritation and/or allergy; post-Inflammatory pigmentation; psoriasis; rosacea; shingles; skin cancers; skin diseases in diabetes mellitus; skin diseases in pregnancy; skin disorders caused by cosmetics such as irritant contact dermatitis and/or allergic contact dermatitis, cosmetic induced pimples (acne), sunscreens allergy, and/or special cosmetic allergies, solar lentigenes; tinea capitis; viral warts; vitiligo; and combinations of these undesirable skin conditions.

In embodiments, compositions in accordance with the present disclosure are suitable for treating diseased skin, or any condition which can result from the excessive amount of pathogens such as fungi, viruses, and or bacterium affecting the skin in any way.

In embodiments, an undesirable skin condition is skin that has a rough texture or uneven appearance such as psoriasis, bumps, razor burns, and/or patches.

The particular concentration in the compositions, generally depends on the purpose for which the composition is to be applied. For example, the dosage and frequency of application can vary depending upon the type and severity of the skin condition. In general, patients are treated by topically applying the hydroquinone, retinoid and multi-metal complex-containing compositions described herein to skin of the décolletage suffering from a condition until the treatment goals are obtained. However, the duration of the treatment can very depending on the severity of the condition. For example, treatments can last several weeks to months depending on whether the goal of treatment is to reduce or eliminate the skin condition.

In treatment embodiments, the compositions and methods in accordance with the present disclosure can be combined with other skin treatment systems. For example, the multi-metallic salt complexes and be applied to skin in combination with skin treatment systems such as the OBAGI NU-DERM® skin treatment system and related Obagi skin care products from O.M.P. Inc. of Long Beach Calif. More specifically copper-zinc malonate compositions can be combined with the OBAGI NU-DERM® skin treatment system in order to promote the beneficial affects of that system. As those skilled in the art will appreciate, the OBAGI NU-DERM® skin treatment system includes the use of a series of products referred to by O.M.P. Inc. as Foaming Gel (Cleanser) or a Gentle Cleanser, a Toner, Clear, EXFODERM® or EXFODERM® Forte, BLENDER®, and Healthy Skin Protection SPF 35 or SUNFADER®. Details regarding these products and the method of using them can be found at the official website of Obagi Medical Products, Inc. The active ingredients and formulations in accordance with the present disclosure may either be incorporated into other product formulations, or applied to the skin before, after, and/or during other skin treatments.

The following non-limiting examples further illustrate compositions and methods in accordance with this disclosure.

EXAMPLE 1

Example 1 below shows suitable ingredients of a reaction mixture for forming copper-zinc malonates for use in the multi-metal complex-containing composition in accordance with the present disclosure.

| Ingredient | Amount |
| --- | --- |
| Malonic acid | 1.8 g |
| cupric carbonate | 0.632 g |
| zinc carbonate | 0.676 g |
| Water | 100 ml |

EXAMPLE 2

1.8 g of malonic acid ($CH_2(COOH)_2$) was combined with 0.632 grams of cupric carbonate ($CuCO_3.Cu(OH)_2$), 0.676 g of zinc carbonate ($3Zn(OH)_2.2ZnCO_3$), and 100 ml of water to form a dispersion. The solution was heated until the reactants went into solution. Well-defined deep-blue crystals precipitated and were separated from the aqueous solution of malonic acid, cupric carbonate, and zinc carbonate (3:1:1 molar ratio) that had been kept at room temperature. Duel salt was formed by replacing acid groups with copper and zinc cations in the same molecule. The deep blue crystals were found to have a melting point of about 210° C.

Sample prepared as per ASTM-D-1971-95 (herein incorporated by reference in its entirety) and analyzed by method 6010 (I.C.P.) (herein incorporated by reference in its entirety) showed 16.5% copper and 12.4% zinc.

EXAMPLE 3

1.8 g of malonic acid ($CH_2(COOH)_2$) was combined with 0.632 grams of cupric carbonate ($CuCO_3.Cu(OH)_2$), 0.676 g of zinc carbonate ($3Zn(OH)_2.2ZnCO_3$), and 100 ml of boiling water. Well-defined deep-blue crystals were separated from the aqueous solution of malonic acid, cupric carbonate, and zinc carbonate (3:1:1 molar ratio) that had been kept at room temperature for 1 week.

EXAMPLE 4

3 moles of malonic acid is thoroughly mixed with 1 mole of copper as cupric carbonate and 1 mole of zinc as zinc carbonate in a stirred tank reactor containing 100 ml of heated water (approximately 95-100° C.). After a short reaction time with cooling, copper-zinc malonate precipitates out of solution with a high yield. A filtration step is used to isolate the complex as a powder. Deep blue crystals are obtained having a melting point of about 210° C.

EXAMPLE 5

In embodiments, copper-zinc malonate formulations suitable for use as the multi-metal complex-containing composition in the present regimens have the following make-up:

| COMPONENT | % BY WEIGHT |
|---|---|
| Copper-zinc malonate* (Active ingredient) | 0.1% |
| Glycerine | 3.0% |
| Propylene Glycol | 25.0% |
| Distilled Water | 71.9% |

EXAMPLE 7

Compositions containing multi-metal complex are prepared having the ingredients listed in Table 4 below in the amounts indicated.

TABLE 2

| Phase | Ingredient | Amount as percentage Of entire emulsion formulation |
|---|---|---|
| Water Phase | Water | 70.656% |
| Water Phase | PEG - 6[1] | 3% |
| Water Phase | Glycerine | 0.5% |
| Water Phase | Methylparaben | 0.2% |
| Water Phase | Phenoxyethanol | .05 |
| Water Phase | Dipropylene glycol | 1.5% |
| Water Phase | Ethylparaben | 0.1% |
| Oil Phase | Isohexadecane[2] | 6.5% |
| Oil Phase | Coco-caprylate/caprate[3] | 3% |
| Oil Phase | $C_{13}$-$C_{15}$ alkane[4] | 3% |
| Oil Phase | Ethylhexyl palmitate | 3% |
| Oil Phase | Lipomulse 165[5] | 2.5% |
| Oil Phase | Cetyl alcohol | 0.5% |
| Oil Phase | Stearyl alcohol | 1.5% |
| Oil Phase | Propylparaben | 0.2% |
| Oil Phase | Butylparaben | 0.05% |
| Oil Phase | Flamenco Satin Green P860[6] | 0.01% |
| Oil Phase | Kobo BPD 500[7] | 0.01% |
| Oil Phase | Coverleaf AR - 80[8] | 0.001% |

[1]Carbowax 300, commercially available from Dow Chemical Company, Midland, MI.
[2]Permethyl 101A, commercially available from Presperse Inc. Somerset, NJ.
[3]Cetiol LC, commercially available from Cognis Chemical, Ambler, PA.
[4]Gemseal 25, commercially available from Presperse Inc. Somerset, NJ.
[5]Commercially available from Lipo Chemicals, Inc., Paterson, NJ.
[6]Commercially available from Engelhard Corporation, Iselin, NJ.
[7]Commercially available from Kobo Products, South Plainfield, NJ.
[8]Commercially available from Presperse Inc. Somerset, NJ.

To prepare the composition, the water phase ingredients are mixed at room temperature (25-35° C.) in a first container. The oil phase ingredients are then combined in a second container with heating to 70-75° C. in a second container. The water phase is then heated to 70-75° C. and added to the oil phase with stirring. The multi-metallic complex prepared in accordance with Example 2 at an amount equivalent to 1.1528% of the entire emulsion is added with stirring at 80° C. Simugel NS at an amount equivalent to 2% of the entire emulsion is added with stirring at 55-60° C. Blueberry extract at an amount equivalent to 0.02% of the entire emulsion is added with stirring at 40-45° C. and the pH is adjusted with a 5% NaOH solution to a pH of 4.2-4.4.

EXAMPLE 8

A randomized controlled study was conducted to evaluate the tolerability of a treatment regimen in accordance with the present disclosure. The treatment regimen included the application of the composition of Example 7, the commercially available OBAGI NU-DERM® BLENDER® containing 2% hydroquinone and tretinoin, either at 0.025% or 0.05%. Forty women in the range of 40 to 60 years old participated in the study, with half of the subjects using 0.025% tretinoin and half of the subjects using 0.05% tretinoin. The tolerability was assessed by the subjects themselves (self-assessment) and by trained clinicians who applied the treatment as discussed below.

Each subject was seen at a clinic everyday (except weekend and holidays when the clinic is closed) from the initial, baseline visit through day 21 to have the morning application treatment system products applied under the supervision and direction of a clinic staff member. Each subject applied the evening application of the treatment system products at home. On weekends and holidays when the clinic was closed each subject applied both the morning and evening application at home.

The order of the morning application of the treatment system products at the clinic was:

1) A "Dime" size amount of the hydroquinone-containing blender was squeezed and a "dime" size amount of the tretinoin onto the palm of the hand and mix together with the fingertip. Then using the fingertips from the opposite hand, the pre-mixed product was applied evenly to the décolletage, and finished by feathering the product up the neck.

2) Two pumps of the multi-metallic complex-containing composition were pumped into the palm of the hand. Using the fingertips from the opposite hand, the entire amount of product was applied to the décolletage, and finished by feathering the product liberally up the neck.

3) Hands were washed after applying the treatment system products and care taken not to touch the eyes or mouth.

The order of the evening application of the treatment system products at home was:

1) A "Dime" size amount of the hydroquinone-containing blender was squeezed out onto the fingertip and applied evenly to the décolletage, and finished by feathering the product up the neck.

2) Two pumps of the multi-metallic complex-containing composition were pumped into the palm of the hand. Using the fingertips from the opposite hand, the entire amount of product was applied to décolletage, and finished by feathering the product liberally up the neck.

3) Hands were washed after applying the treatment system products with care to avoid touching the eyes or mouth area.

At least 8 hours were allowed between the morning and evening applications.

Both treatment regimens were well tolerated by the subjects, with the 0.025% tretinoin regimen being better tolerated than the 0.05% tretinoin regimen.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of treating skin comprising:
    administering to an area of skin a first treatment and, after a predetermined period of time, a second treatment,
    the first treatment comprising topically applying a retinoid, a hydroquinone, and a multi-metal complex;
    the second treatment comprising topically applying a hydroquinone and a multi-metal complex
    wherein the multi-metal complex employed in the first treatment and in the second treatment comprises a central malonate unit, wherein the central malonate unit bridges one or more copper molecules and one or more zinc molecules by coordinate bonding.

2. The method according to claim 1, further comprising the step of waiting at least four hours between the first treatment and the second treatment.

3. The method according to claim 1, wherein the first treatment occurs in the morning.

4. The method according to claim 3, wherein the second treatment occurs in the evening.

5. The method according to claim 1, wherein the first treatment occurs in the evening.

6. The method according to claim 1, further comprising sequentially applying the retinoid, the hydroquinone, and the multi-metal complex of the first treatment.

7. The method according to claim 1, further comprising pre-mixing the retinoid and the hydroquinone of the first treatment substantially immediately prior to administering the first treatment to the area of skin.

8. A method comprising:
    pre-mixing a retinoid with a hydroquinone-containing composition to form a pre-mixed formulation;
    applying the pre-mixed formulation to the skin; and
    applying a composition comprising a multi-metal complex to the skin
    wherein the multi-metal complex comprises a central malonate unit, wherein the central malonate unit bridges one or more copper molecules and one or more zinc molecules by coordinate bonding.

9. The method according to claim 8, wherein the pre-mixed formulation is applied to the skin prior to the composition comprising the multi-metal complex.

10. A method of treating skin comprising:
    topically applying a retinoid and a hydroquinone to an area of non-facial skin; and
    topically applying a composition comprising at least one multi-metal complex to the area of non-facial skin previously treated with retinoid and hydroquinone, wherein the multi-metal complex comprises a central malonate unit, wherein the central malonate unit bridges one or more copper molecules and one or more zinc molecules by coordinate bonding.

11. The method according to claim 10, wherein the area of non-facial skin is the décolletage.

12. The method according to claim 10, wherein the retinoid and hydroquinone are sequentially applied to the area of non-facial skin.

13. The method according to claim 10, wherein the retinoid and hydroquinone are simultaneously applied to the area of non-facial skin.

14. The method according to claim 10, wherein the retinoid is retinol.

15. The method according to claim 10, wherein the retinoid is tretinoin.

16. The method according to claim 10, wherein the hydroquinone is arbutin.

17. A method of treating skin comprising:
    topically applying a retinoid and a hydroquinone to an area of non-facial skin; and
    topically applying a composition comprising at least one multi-metal complex to the area of non-facial skin previously treated with retinoid and hydroquinone, wherein the multi-metal complex comprises a central unit, wherein the central unit is derived from at least one compound selected from polycarboxylic acids and amino acids having at least two carboxylic acid groups and the center unit bridges one or more copper molecules and one or more zinc molecules by coordinate bonding.

18. A method of treating skin comprising:
    topically applying a retinoid and a hydroquinone to an area of non-facial skin; and
    topically applying a composition comprising at least one multi-metal complex to the area of non-facial skin previously treated with retinoid and hydroquinone, wherein the multi-metal complex comprises a reaction product of a compound having two or more carboxylic acid groups with basic salts of two or more coordination elements selected from one or more of copper, silver, gold, aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium, wherein the two or more coordination elements are joined to a central unit derived from the compound having two or more carboxylic acid groups.

* * * * *